United States Patent [19]
Aita et al.

[11] Patent Number: 5,885,272
[45] Date of Patent: Mar. 23, 1999

[54] SYSTEM AND METHOD FOR PERCUTANEOUS MYOCARDIAL REVASCULARIZATION

[76] Inventors: Michael Aita, 1043 Payette, Sunnyvale, Calif. 94807; Gene Samson, 262 Selwyn Dr., #1, Milpitas, Calif. 95035; Bruce H. Wand, 4193 Mystic Ct., San Jose, Calif. 95124; Robert F. Kotmel, 436 W. Bayview, Sunnyvale, Calif. 94806

[21] Appl. No.: 561,526

[22] Filed: Nov. 21, 1995

Related U.S. Application Data

[63] Continuation of Ser. No. 368,409, Dec. 30, 1994, abandoned, which is a continuation of Ser. No. 78,443, Jun. 15, 1993, abandoned, which is a division of Ser. No. 23,161, Feb. 25, 1993, Pat. No. 5,389,096, which is a continuation of Ser. No. 630,258, Dec. 18, 1990, abandoned, and a continuation-in-part of Ser. No. 605,658, Oct. 30, 1990, Pat. No. 5,093,877.

[51] Int. Cl.$^6$ .................................................. A61B 17/36
[52] U.S. Cl. .............................................. 606/7; 128/898
[58] Field of Search .................................. 606/7, 10–19; 607/88, 89; 128/898

[56] References Cited

U.S. PATENT DOCUMENTS

| | | |
|---|---|---|
| 3,456,211 | 7/1969 | Koester . |
| 3,932,184 | 1/1976 | Cohen et al. . |
| 4,147,402 | 4/1979 | Chown . |
| 4,266,548 | 5/1981 | Davi . |
| 4,273,109 | 6/1981 | Enduby . |
| 4,290,667 | 9/1981 | Chown . |
| 4,380,365 | 4/1983 | Gross . |
| 4,398,790 | 8/1983 | Righini . |
| 4,538,609 | 9/1985 | Takehara et al. . |
| 4,543,090 | 9/1985 | McCoy . |
| 4,658,817 | 4/1987 | Hardy ........................................... 606/7 |
| 4,669,467 | 6/1987 | Willett et al. ................................ 606/7 |
| 4,676,231 | 6/1987 | Hisazumi et al. . |

(List continued on next page.)

FOREIGN PATENT DOCUMENTS 0058406  3/1988  Japan .

OTHER PUBLICATIONS

"Intraluminal Ultrasound Guidance of Transverse Laser Coronary Atherectomy," H. T. Aretz, M. A. Martinelli, E. G. LeDet., T. Sedlacek, G. F. Hatch, and R. E. Gregg, SPIE vol. 1201 Optical Fibers in Medicine V (1990).

Mirhoseini, et al., Clinical Report: "Laser Myocardial Revascularization," Lasers in Surgery and Medicine 6:459–461 (1986).

Mirhoseini, et al., "Myocardial Revascularization by Laser: A Clinical Report," Lasers in Surgery and Medicine 3:241–245 (1983).

Mirhoseini, et al., "Revascularization of the Heart by Laser," Journal of Microsurgery 253–260 (Jun. 1981).

Mirhoseini, "Laser Applications in Thoracic and Cardiovascular Surgery," Medical Instrumentation, vol. 17, No. 6, 401–403 (Nov.–Dec. 1982).

(List continued on next page.)

*Primary Examiner*—Michael Peffley

[57] ABSTRACT

A method and apparatus are described for percutaneous myocardial revascularization of a human heart. A deflectable elongated flexible lasing apparatus is used which includes a source of laser radiation, an elongated flexible radiation conveying member for conducting the laser radiation to a lens on the distal end of the radiation conveying member for focusing the laser radiation, and control lines for deflecting the distal end of the radiation conveying member. The control lines are secured to the distal end of the radiation conveying member for changing the angle of deflection of the distal end of the radiation conveying member. The lasing apparatus is guided to an area within the patient's heart, and the distal end of the lasing apparatus is directed to an area of interest where the inner wall of the heart is irradiated with laser energy to form a channel through the myocardium for a desired distance. In a preferred embodiment, channels are formed without perforating the epicardium of the heart.

5 Claims, 2 Drawing Sheets

U.S. PATENT DOCUMENTS

| | | |
|---|---|---|
| 4,678,268 | 7/1987 | Russo et al. . |
| 4,693,556 | 9/1987 | McCaughan, Jr. . |
| 4,832,023 | 5/1989 | Murphy-Chutorian et al. . |
| 4,832,024 | 5/1989 | Boussignac et al. . |
| 4,842,390 | 6/1989 | Sottini et al. . |
| 4,844,580 | 7/1989 | Lynch et al. . |
| 4,850,351 | 7/1989 | Herman et al. . |
| 4,860,172 | 8/1989 | Schlager . |
| 4,878,725 | 11/1989 | Hessel et al. . |
| 4,913,142 | 4/1990 | Kittrell et al. . |
| 4,913,510 | 4/1990 | Lynch et al. . |
| 4,917,084 | 4/1990 | Sinofsky . |
| 4,967,745 | 11/1990 | Hayes et al. . |
| 4,985,028 | 1/1991 | Isner et al. ............................ 606/15 |
| 4,985,029 | 1/1991 | Hoshino . |
| 4,997,431 | 3/1991 | Isner et al. . |
| 5,041,109 | 8/1991 | Abela . |
| 5,061,265 | 10/1991 | Abela et al. ............................ 606/7 |
| 5,093,877 | 3/1992 | Aita et al. ............................ 606/15 |
| 5,106,386 | 4/1992 | Isner et al. . |
| 5,109,830 | 5/1992 | Cho . |
| 5,125,926 | 6/1992 | Rudko et al. ............................ 606/19 |
| 5,167,686 | 12/1992 | Wong . |
| 5,200,604 | 4/1993 | Rudko et al. ............................ 606/18 |
| 5,380,316 | 1/1995 | Aita et al. ............................ 606/7 |
| 5,389,096 | 2/1995 | Aita et al. ............................ 606/15 |

OTHER PUBLICATIONS

Mirhoseini, "Laser Revascularization of the Heart," in New Frontiers in Laser Medicine and Surgery (Atsumi, Editor), ISBN Elsevier Science Publishing Co., 296–303 (1982).

Desilets—Hoffman, United States Catheter and Instrument Corporation, Jul. 1965.

Mirhoseini, et al., "Transvernicular Revascularization by Laser," Lasers in Surgery and Medicine 2:187–198 (1982).

Jeevanandam, et al., "Myocardial Revascularization by Laser–Induced Channels," Surgical Forum XLI, 225–227 (Oct. 1990).

Hardy, et al., "Regional Myocardial Blood Flow and Cardiac Mechanics in Dog Hearts With Co2 Laser–Induced Intramyocardial Revascularization," Basic Res. Cardiol. 85:179–197 (1990).

Mirhoseini, et al., "Clincal and Histological Evaluation of Laser Myocardial Reascularization," Journal of Clinical Laser Medicine & Surgery, 73–78 (Jun. 1990).

Mirhoseini, et al., "Lasers in Cardiothoracic Surgery," in Lasers in General Surgery (Joffe, Ediotr), Williams and Wilkins, 216–232 (1989).

Mirhoseini, et al., "New Concepts in Revascularization of the Myocardium," A Thorac. Surg. 45:415–420 (Apr. 1988).

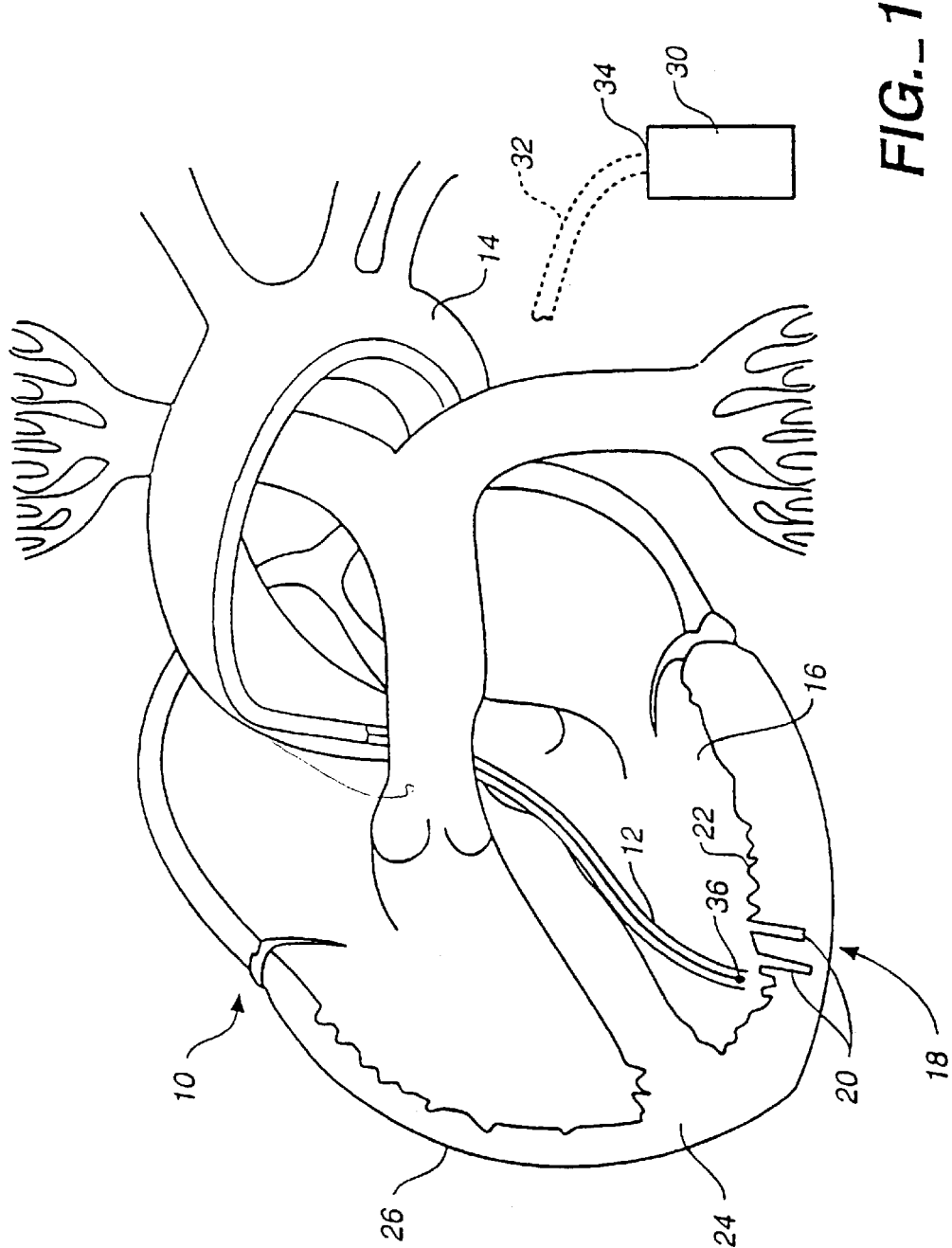
FIG._1

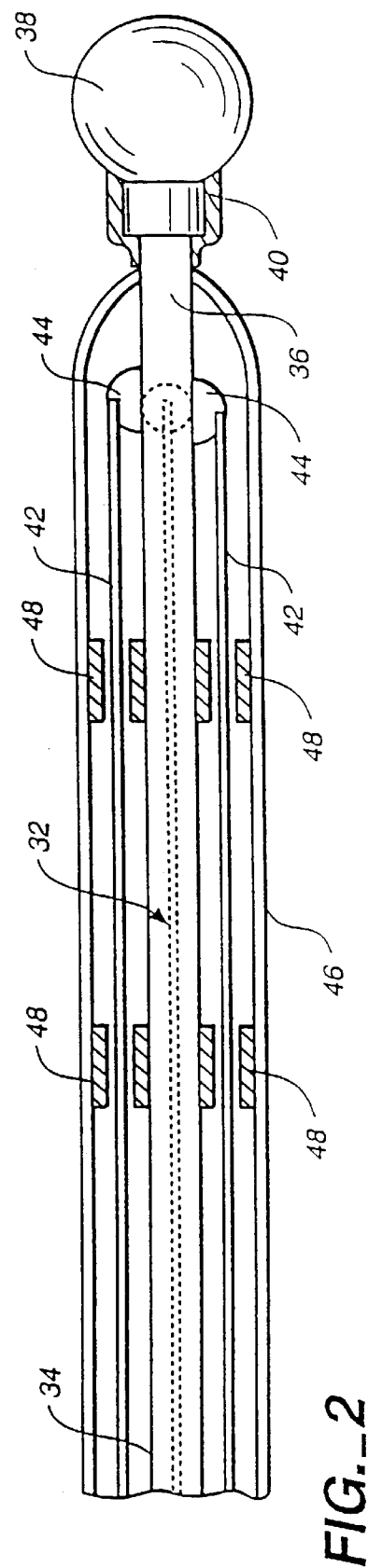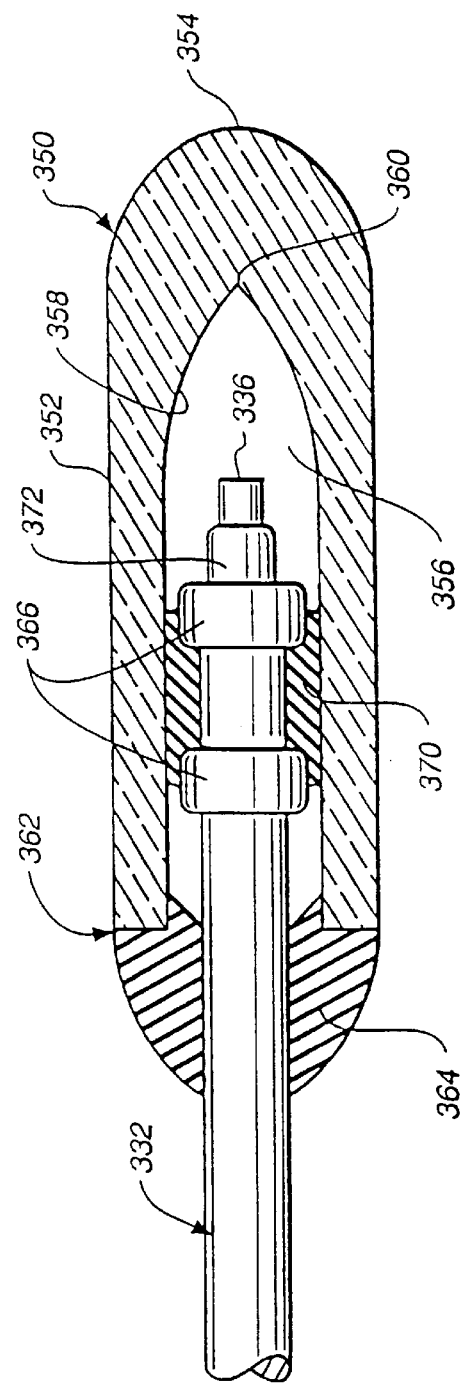

SYSTEM AND METHOD FOR PERCUTANEOUS MYOCARDIAL REVASCULARIZATION

This is a continuation application of application Ser. No. 08/368,409 which was filed on Dec. 30, 1994 (now abandoned), which is a continuation of Ser. No. 08/078,443, filed Jun. 15, 1993 (now abandoned), which is a divisional of 08/023,161, filed Feb. 25, 1993, now U.S. Pat. No. 5,387,096, which is a continuation of Ser. No. 07/630,258, filed Dec. 18, 1990 (now abandoned) and a continuation-in-part of Ser. No. 07/605,658, filed Oct. 30, 1990, now U.S. Pat. No. 5,093,877.

FIELD OF THE INVENTION

This invention is generally directed to the field of laser surgery, and more particularly to laser surgery procedures to improve the flow of blood to the heart muscle.

BACKGROUND OF THE INVENTION

The number and variety of medical methods available to repair the effects of cardiovascular disease has increased rapidly over the last several years. More particularly, alternatives to open heart surgery and cardiovascular by-pass surgery have been extensively investigated, resulting in non-surgical procedures such as percutaneous transluminal coronary angioplasty, laser angioplasty, and atherectomy. These procedures are primarily directed toward the reduction of stenosis within the vasculature of a patient by either expanding the lumen through the use of a balloon, or ablating or otherwise removing the material making up the stenosis.

While these procedures have shown considerable promise, many patients still require bypass surgery due to such conditions as the presence of extremely diffuse stenotic lesions, the presence of total occlusions and the presence of stenotic lesions in extremely tortuous vessels. Also, some patients are too sick to successfully undergo bypass surgery, and because the above treatments require surgical backup in the case of complications, they are untreatable. Some patients requiring repeat bypass surgeries are also untreatable.

One alternative to these procedures is known as Laser Myocardial Revascularization (LMR). In LMR, channels are formed in the heart wall with a laser. These channels provide blood flow to ischemic heart muscle. A history and description of this method is presented by Dr. M. Mirhoseini and M. Cayton in "Lasers in Cardiothoracic Surgery" in *Lasers in General Surgery* (Williams & Wilkins; 1989) pp. 216–223.

In the procedure described therein, a $CO_2$ laser is used to produce channels in the heart wall from the epicardium through the endocardium. This procedure follows a surgical cutdown. External pressure is used to stop bleeding from the interior of the heart to the outside. Dr. Mirhoseini has documented that although the channel is sealed at the epicardial layer, it remains patent in the endocardial and myocardial layers. Laser energy is transmitted from the laser to the epicardium by means of an articulated arm device that is commonly used for $CO_2$ laser surgery.

A proposed improvement in the design is described in Hardy—U.S. Pat. No. 4,658,817. A needle is added to the distal tip of the articulated arm system, with laser energy passing through the lumen of the needle. The metal tip of the needle of the device is used to pierce most of the myocardium and the laser beam is used to create the desired channel through the remaining portion of the myocardium and through the adjacent endocardium.

Hardy contends that mechanical piercing serves to facilitate sealing of the epicardial portion of the channel. Mechanical piercing is highly undesirable, because such piercing always entails some degree of tearing of the pierced tissue. Tearing leads to fibrosis as the mechanical tear heals. Fibrosis severely diminishes the effectiveness of the LMR treatment.

These LMR procedures still require that the chest wall be opened in order to access the heart muscle with presently utilized laser devices. Thus these procedures require major surgery which is highly invasive and which may result in severe complications.

An additional problem associated with those procedures utilizing an articulated arm device is that the articulated arm is difficult to manipulate. Thus portions of the heart may be effectively unreachable by the device.

Broadly, it is the object of the present invention to provide an improved apparatus and method for performing laser myocardial revascularization.

It is a further object of the present invention to provide an apparatus and method for performing laser myocardial revascularization which can be performed percutaneously.

It is a still further object of the present invention to provide an apparatus and method for performing laser myocardial revascularization which can access difficult to reach portions of the heart.

It is a yet further object of the present invention to provide an apparatus and method for performing laser myocardial revascularization which allow for monitoring of the creation of the percutaneously created channels.

These and other objects of the present invention will be apparent to those skilled in the art from the following detailed description and the accompanying drawings.

SUMMARY OF THE INVENTION

The apparatus of the present invention comprises an elongated flexible lasing apparatus. The apparatus includes a source of laser radiation. The apparatus also includes an elongated flexible radiation conveying means having proximal and distal ends. In the preferred embodiment of the invention, the radiation conveying means comprises an optical fiber. The radiation conveying means is operatively connected to the source of laser radiation to receive the laser radiation and conduct the laser radiation to be emitted at the distal end. The lasing apparatus also includes lens means at the distal end of the radiation conveying means for controlling the laser radiation emitted from the distal end of the radiation conveying means. The lasing apparatus further includes means for guiding the distal end of the radiation conveying means through the vasculature of a patient and positioning that distal end so as to direct the laser radiation upon a fixed portion of tissue. In the preferred embodiment, the lasing apparatus is disposed within a steerable or deflectable guiding catheter.

In a preferred embodiment of the present invention, the means for guiding the distal end of the radiation conveying means comprises a plurality of control lines having proximal and distal ends. Those distal ends are secured at the distal end of an optical fiber laser apparatus. The guiding means further includes means at the proximal ends of the control lines for axially moving the control lines. The axial movement changes the angle of the distal end of the optical fiber with respect to the proximal end of the optical fiber.

The method of the present invention comprises a method of percutaneous myocardial revascularization of the myocardium of the heart of a patient. The method includes the step of inserting a guidable elongated flexible lasing apparatus into a patient's vasculature. The distal end of the lasing apparatus is guided to an area in the heart to be revascularized. Then the inner wall of the heart is irradiated with laser energy emitted from the distal end of the lasing apparatus. This irradiation is performed with sufficient energy and for a sufficient time to cause a channel to be formed from the endocardium into the myocardium for a desired distance.

In alternative embodiments of the present invention, the elongated flexible radiation conveying lasing means comprises an optical waveguide suitable for use with a $CO_2$ or other laser.

BRIEF DESCRIPTION OF THE DRAWINGS

FIG. 1 is a schematic section of a human heart showing revascularization of the myocardium according to the invention.

FIG. 2 is a schematic cross-section of a deflectable lasing apparatus embodying the features of the invention.

FIG. 3 is a cross-section of a preferred lens design for the invention.

DETAILED DESCRIPTION OF THE PREFERRED EMBODIMENT

As is shown in the drawings, which are provided for purposes of illustration and not by way of limitation, the apparatus of the present invention is embodied in a system for revascularization of the myocardium of a human heart 10. As is illustrated in FIG. 1, the deflectable elongated flexible lasing apparatus 12 is inserted into the vasculature of a patient, generally through one of the major vessels 14, thereby affording access for the apparatus to an area such as a ventricle 16 having an area 13 in need of increased blood circulation due to cardiovascular disease. Portions of the heart other than the ventricles might also be revascularized by this method. A number of channels 20 can be formed by lasing apparatus 12 from the inner wall, or endocardium 22, and extend a desired distance through the myocardium 24 without perforating the exterior of the heart wall, the epicardium 26.

Lasing apparatus 12 includes a remotely located source of laser energy 30 connected to the proximal end 34 of an elongated flexible radiation conveying means, which in the preferred embodiment comprises an optical fiber 32. Laser 30 may typically be an HO YAG laser, for example, although other sources of energy, such as excimer lasers, are adaptable to the invention. Optical fiber 32 conducts the laser energy to its distal end 36. Optical fiber 32 may, in a preferred embodiment, be approximately 240 microns in diameter. This diameter optical fiber has the required flexibility for passage through the vasculature, and yet may be reinforced in a variety of ways to prevent breakage.

It will be apparent to those skilled in the art that a $CO_2$ laser may be used as laser 30 if a suitable optical fiber or waveguide is used as its radiation conveying means. While the discussion hereafter refers to optical fiber devices, the present invention is not limited to that particular implementation of a radiation conveying means.

Referring to FIG. 2, a lens 38 having a sleeve 40, is preferably connected to the distal end 36 of optical fiber 32. Although lens 38 is illustrated in FIG. 2 as being a ball type lens, the preferred embodiment of lens 38 is illustrated in FIG. 3 which is discussed below. Lens 38 focuses and concentrates the laser energy emitted by optical fiber 32.

Optical fiber 32 may be housed in a catheter which may incorporate one or more other functions in addition to the housing of optical fiber 32. The catheter may, for example, also provide for a guidewire over which the catheter may be advanced. The present invention is also adaptable to a guiding catheter used to initially position the catheter which houses optical fiber 32.

In one preferred embodiment of the present invention, a plurality of control lines 42 are connected at their distal ends to the distal end 36 of optical fiber 32, such as by adhesive bonding 44. Adhesive bonding 44 may utilize any of a variety of adhesives. At least two, and preferably four, control lines 42 are thus axially, and preferably symmetrically, disposed on optical fiber 32. Axial movement of control lines 42 will thus change the angle of deflection of distal end 36 of optical fiber 32 with respect to its proximal end 34. Means (not shown) such as a ring or knob may be attached to the proximal ends of control lines 42 to allow manipulation of control lines 42. Control lines 42 are preferably approximately 3-mil stainless steel wire, but may be similar diameter filaments, such as nylon, or other suitable materials.

In addition, an outer tubular member 46 preferably encloses control lines 42 and optical fiber 32, forming a protective covering. Outer tubular member 46 is secured at its distal end to distal end 36 of optical fiber 32, rearward of lens 38. In order to facilitate precise control of the tip during the procedure, control lines 42 are routed through spaced apart channels 48 that are attached to the outer surface of optical fiber 32. Channels 48 are preferably constructed of 30 gauge polyamide tubing. Control lines 42 are thus guided to remain both separated and within well controlled areas on the exterior of optical fiber 32, thus allowing for the accurate guidance of the catheter through the remote manipulation of control lines 42.

Referring to FIG. 3, it has been found that in a preferred embodiment of the invention, a lens 350 is configured to include an essentially cylindrical outer surface 352 terminating in a convex distal tip 354. An optical fiber 332 extends into an internal cavity 356 and terminates in a position spaced apart from an internal aspheric or ogival shaped surface 358, the cavity apex 360 of which is distal from distal end 336 of fiber 332. The interface 362 between optical fiber 332 and lens 350 is reinforced, preferably with epoxy 364 or the like, although other means of reinforcement designed to prevent dislodging of the lens are adaptable to the invention.

Optical fiber 332 may also be provided with one or more photo-opaque gold bands 366 located so as to provide an indication of the location of the probe on a fluoroscope or the like. Optical fiber 332 may be secured in the cavity by an adhesive 370, such as epoxy or the like, and the polyamide coating 372 of optical fiber 332 may be removed at the distal end to improve the optical qualities of the lens.

The basic method of the present invention has been laid out above. Lasing apparatus 12 is inserted into the vasculature of a patient, generally through one of the major vessels 14, thereby affording access for the apparatus to an area such as a ventricle 16 having an area 18 in need of increased blood circulation due to cardiovascular disease. A number of channels 20 can be formed by lasing apparatus 12 from the inner wall, or endocardium 22, and extend a desired distance through the myocardium 24 without perforating the exterior of the heart wall, the epicardium 26.

In operation, the distal end of lasing apparatus 12 may be maintained in position on the inner heart wall 22 by a gentle pressure, to insure that lasing apparatus 12 is not dislodged in the formation of the channel between pulses of the laser. Such pressure can be applied either by pushing the catheter forward into the tissue or by applying a vacuum at the distal tip 36 of lasing apparatus 12. The heart beat is preferably monitored, and the laser is preferably gated to generate one or more pulses during contractions (systole) of the heart, and to generate no pulses during the rest of the heart cycle. These procedures combines to anchor lasing apparatus 12 to a relatively stable location on the tissue that is to be ablated.

It has been found that the heart muscle is much more dense near the exterior surface and thus the cutting occurs fairly rapidly for a given laser energy output in the myocardium and diminishes as the exterior portion of the heart known as the epicardium is approached. Thus, the person conducting the procedure can accurately determine the amount of revascularization by the speed with which the catheter progresses. The probe cuts while in contact, so tactile sense is preserved. This permits termination of the cutting of a given channel prior to the piercing of the exterior of the heart muscle.

Another method of guiding the lasing apparatus into a proper position within the heart is to place the lasing apparatus 12 within a deflectable guiding catheter (not shown) having x-y steerability, for an added degree of steerability and control of the lasing apparatus. In practice, the positioning of the device may be viewed by esophageal ultrasound imaging or fluoroscope imaging. It may also be desirable to add one or more radiopaque marker bands to the distal portion 36 of lasing apparatus 12, for fluoroscopic imaging. Lasing apparatus 12 may thereby be aimed and controlled for forming channels 20 in the myocardium of the heart for revascularization of areas of the heart in need of improved blood flow.

In early experiments with an HO laser, it was found that it may be desirable to begin the procedure with approximately 0.65 j pulses, at a frequency of at least 2 Hz, in order to penetrate the endocardium, and then decrease the laser power to approximately 0.2 j to form the channel in the myocardium. This minimizes the need for anchoring the catheter to the area to be treated. Note that the dosimetry is dependent upon the diameter of the lens used.

In practice, it has been found that lens 350 of the embodiment of FIG. 3, when in contact with tissue, cuts a lumen equal or greater than the lens diameter which is in front of and axially aligned with the axis of the lens. This provides improved ablation into the heart muscle of channels of the type preferred in this method. As the channel is cut, the cylindrical outer surface 352 assists in guiding and controlling the catheter during the cutting process. The angle of the projected energy from the lens can also be controlled by some degree with the separation of distal tip 336 of optical fiber 332 from the cavity distal apex 360. It has also been found that the construction is scalable.

It has been found that channels that are approximately 1.5 mm–2.0 mm in diameter and approximately 1 to 3 cm deep may easily and efficiently be cut by this method, and that the revascularization procedure dramatically improves the flow of blood to the heart muscle, thereby decreasing the probability of heart attack from occlusion of the external vasculature of the heart.

The method of the present invention overcomes the difficulty of achieving the fine precision required in laser angioplasty and is useful for patients with advanced disease or with vasculature who might not otherwise be candidates for angioplasty procedures. It is evident that the method and apparatus for myocardial revascularization overcomes problems of spasm and occlusion of blood vessels supplying the heart, and that myocardial revascularization offers a valuable alternative form of treatment of heart disease which may be used separately or in conjunction with other treatments. In addition, the present invention may be suitable for those too sick for bypass surgery, as well as for those patients with myocardium at risk.

There has been described herein an elongated flexible lasing apparatus and method for percutaneous myocardial revascularization. Various modifications to the present invention will become apparent to those skilled in the art from the foregoing description and accompanying drawings. Accordingly, the present invention is to be limited solely by the scope of the following claims.

What is claimed is:

1. A minimally invasive procedure for ablating tissue in a region of a ventricular wall of a patient's heart which defines in part a chamber therein, comprising:

a) disposing a tubular delivery catheter within the patient's vasculature which has proximal and distal ends, a port in the distal end, an inner lumen extending therein to and in fluid communication with the port in the distal end and a distal extremity disposed within the heart chamber;

b) providing an elongated flexible ablation device which has an elongated ablation energy transmitting member with proximal and distal ends and a surface on the distal end to emit ablation energy in the form transmitted through the ablation energy transmitting member to ablate tissue;

c) disposing the elongated flexible ablation device within the inner lumen of the tubular delivery catheter so that the distal end of the ablation energy transmitting member is disposed adjacent to a region of the patient's heart wall in which tissue is to be ablated;

d) contacting the ventricular wall of the patient's heart with the ablation energy emitting surface on the distal end of the elongated flexible ablation device; and e) ablating myocardial tissue in the ventricular wall by said ablation energy emitted from the emitting surface while the emitting surface contacts the ventricular wall.

2. The procedure of claim 1 wherein the elongated device ablates tissue in the free ventricular wall at a plurality of locations.

3. The procedure of claim 1 wherein the tissue is ablated by the emission of radiation from the distal end of the ablation device which penetrates into the myocardium of the free ventricular wall.

4. The procedure of claim 3 wherein the radiation is laser energy.

5. A minimally invasive procedure for forming a channel into a myocardial layer of a ventricular wall of a patient's heart which defines in part a chamber therein, comprising:

a) providing an assembly having
       a tubular delivery member with a distal end, a port in the distal end and an inner lumen extending therein to and in fluid communication with the port in the distal end, and
       an elongated flexible laser device disposed with the inner lumen of the tubular delivery member having proximal and distal ends and a surface on the distal end thereof to emit laser energy;

b) introducing the tubular delivery member into the patient and advancing the tubular delivery member therein until the distal end thereof is adjacent to the free ventricular wall;

c) advancing the elongated flexible laser device within the inner lumen of the tubular delivery member until the laser energy emitting surface contacts a surface of the ventricular wall; and d) emitting laser energy from the laser energy emitting surface on the distal end of the laser device onto a surface of the endocardium of the ventricular wall while the emitting surface is in contact therewith at sufficient power levels to form a channel into.

* * * * *